US010724017B1

(12) United States Patent
Kutyavin et al.

(10) Patent No.: US 10,724,017 B1
(45) Date of Patent: Jul. 28, 2020

(54) INHIBITION OF DNA POLYMERASES BY URACIL-DNA GLYCOSYLASE-CLEAVABLE OLIGONUCLEOTIDE LIGANDS

(71) Applicant: Cepheid, Sunnyvale, CA (US)

(72) Inventors: Igor V. Kutyavin, Woodinville, WA (US); Sergey G. Lokhov, Bothell, WA (US)

(73) Assignee: Cepheid, Sunnyvale, CA (US)

( * ) Notice: Subject to any disclaimer, the term of this patent is extended or adjusted under 35 U.S.C. 154(b) by 0 days.

(21) Appl. No.: 16/210,643

(22) Filed: Dec. 5, 2018

Related U.S. Application Data

(60) Provisional application No. 62/595,547, filed on Dec. 6, 2017.

(51) Int. Cl.
| | |
|---|---|
| *A61K 48/00* | (2006.01) |
| *C07H 21/04* | (2006.01) |
| *C12N 9/12* | (2006.01) |
| *C12N 15/113* | (2010.01) |
| *C12N 15/115* | (2010.01) |
| *C12Q 1/686* | (2018.01) |
| *C12N 9/99* | (2006.01) |

(52) U.S. Cl.
CPC ............. *C12N 9/1252* (2013.01); *C12N 9/99* (2013.01); *C12N 15/113* (2013.01); *C12N 15/115* (2013.01); *C12Q 1/686* (2013.01); *C12N 2310/16* (2013.01); *C12N 2310/531* (2013.01); *C12Y 207/07007* (2013.01)

(58) Field of Classification Search
CPC ...................................................... A61K 45/06
See application file for complete search history.

(56) References Cited

U.S. PATENT DOCUMENTS

| | | | |
|---|---|---|---|
| 3,721,725 | A | 3/1973 | Briggs |
| 4,683,195 | A | 7/1987 | Mullis |
| 4,683,202 | A | 7/1987 | Mullis |
| 5,270,184 | A | 12/1993 | Walker |
| 5,693,502 | A | 12/1997 | Gold |
| 5,801,155 | A | 9/1998 | Kutyavin |
| 5,824,517 | A | 10/1998 | Cleuziat |
| 5,854,033 | A | 12/1998 | Lizardi |
| 6,063,603 | A | 5/2000 | Davey |
| 6,127,121 | A | 10/2000 | Meyer, Jr. |
| 6,214,587 | B1 | 4/2001 | Dattagupta |
| 6,251,639 | B1 | 6/2001 | Kurn |
| 6,410,278 | B1 | 6/2002 | Notomi |
| 7,794,945 | B2 | 9/2010 | Hedgpeth |
| 8,143,006 | B2 | 3/2012 | Kutyavin |
| 8,349,556 | B2 | 1/2013 | Kutyavin |

OTHER PUBLICATIONS

Jayasena, S.D., "Aptamers: An Emerging Class of Molecules That Rival Antibodies in Diagnostics," Clinical Chemistry 45(9):1628-1650, Sep. 1999.
Martin, F.H., et al., "Base Pairing Involving Deoxyinosine: Implications for Probe Design," Nucleic Acids Research 13(24):8927-8938, Dec. 20, 1985.
Skerra, A., "Phosphorothioate Primers Improve the Amplification of DNA Sequences by DNA Polymerases With Proofreading Activity," Nucleic Acids Research 20(14):3551-3554, Jul. 25, 1992.
Yakimovich, O.Y., "Influence of DNA Aptamer Structure on the Specificity of Binding to Taq DNA Polymerase," Biochemistry (Moscow) 68(2):228-235, Feb. 2003.
Yao, M., and Y.W. Kow, "Further Characterization of *Escherichia coli* Endonuclease V. Mechanism of Recognition for Deoxyinosine, Deoxyuridine, and Base Mismatches in DNA" The Journal of Biological Chemistry 272 (49):30774-30779, Dec. 5, 1997.
Yoshizawa, S., "Nuclease Resistance of an Extraordinarily Thermostable Mini-Hairpin DNA Fragment, d (GCGAAGC) and its Application to In Vitro Protein Synthesis," Nucleic Acids Research 22(12):2217 2221, Jun. 25, 1994.

*Primary Examiner* — Amy H Bowman
(74) *Attorney, Agent, or Firm* — Barry L. Davison; Davis Wright Tremaine LLP

(57) ABSTRACT

Provided are methods and compositions for activating oligonucleotide aptamer-deactivated DNA polymerases, comprising modifying the aptamer by uracil-DNA glycosylase enzymatic activity to reduce or eliminate binding of the oligonucleotide aptamer to the DNA polymerase, thereby activating DNA synthesis activity of the DNA polymerase in a reaction mixture. Mixtures for use in methods of the invention are also provided. In some aspects, the oligonucleotide aptamers are circular and comprise one or more deoxyuridine nucleotides providing for aptamer-specific recognition and modification of the circular aptamer by the uracil-DNA glycosylase enzymatic activity. Exemplary oligonucleotide aptamers, mixtures and methods employing uracil-DNA glycosylase enzymatic activity are provided. The methods can be practiced using kits comprising a DNA polymerase-binding oligonucleotide aptamer and at least one uracil-DNA glycosylase enzymatic activity having oligonucleotide aptamer-specific recognition to provide for specific modification of the aptamer by the uracil-DNA glycosylase enzymatic activity.

13 Claims, 7 Drawing Sheets

Specification includes a Sequence Listing.

```
         C G T T                            C G T T
        G     T TCGCTTTAAATCGCGCA          G     T TCGCTTTAAATCGCGCA T 3'
        A    T                 T 3'        A    T                   T
           T C T  AGCGAAATTTAGCGCGT           T C U  AGCGAAATTTAGCGCGT 5'
                                  5'
              SEQ ID NO:5                         SEQ ID NO:7

C G U T                            C G T U
        G     T TCGCTTTAAATCGCGCA          G     T TCGCTTTAAATCGCGCA T 3'
        A    T                 T 3'        A    T                   T
           T C T  AGCGAAATTTAGCGCGT           T C T  AGCGAAATTTAGCGCGT 5'
                                  5'
              SEQ ID NO:9                         SEQ ID NO:11
```

```
         C G T T                            C G T T
        G     T TCGCTTTAAATCGCGCA          G     T TCGCTTTAAATCGCGCA T 3'
        A    T                 T 3'        A    T                   T
           T T C U  AGCGAAATTTAGCGCGT         T U C T  AGCGAAATTTAGCGCGT 5'
                                  5'
              SEQ ID NO:6                         SEQ ID NO:8

C G U T                            C G T U
        G     T TCGCTTTAAATCGCGCA          G     T TCGCTTTAAATCGCGCA T 3'
        A    T                 T 3'        A    T                   T
           U T C T  AGCGAAATTTAGCGCGT         T T C U  AGCGAAATTTAGCGCGT 5'
                                  5'
              SEQ ID NO:10                        SEQ ID NO:12
```

Figure 2

| Aptamer number | Aptamer linear sequence | Aptamer in circular form |
|---|---|---|
| SEQ ID NO:13 | pAAATTATATTCTTAGCGTTTTATAATTTTAAAACGAAGTTTTA | (hairpin structure) |
| SEQ ID NO:14 | pAAATTATAUTCTTAGCGTTTTATAATTTTAAAACGAAGTTTTA | (hairpin structure) |
| SEQ ID NO:15 | pAAATTATATUCTTAGCGTTTTATAATTTTAAAACGAAGTTTTA | (hairpin structure) |
| SEQ ID NO:16 | pAAATTATATTCUTAGCGTTTTATAATTTTAAAACGAAGTTTTA | (hairpin structure) |
| SEQ ID NO:17 | pAAATTATATTCTUAGCGTTTTATAATTTTAAAACGAAGTTTTA | (hairpin structure) |
| SEQ ID NO:18 | pAAATTATATTCTTAGCGUTTTATAATTTTAAAACGAAGTTTTA | (hairpin structure) |
| SEQ ID NO:19 | pAAATTATATTCTTAGCGTUTTATAATTTTAAAACGAAGTTTTA | (hairpin structure) |
| SEQ ID NO:20 | pAAATTATATTCTTAGCGTTUTATAATTTTAAAACGAAGTTTTA | (hairpin structure) |

Figure 4

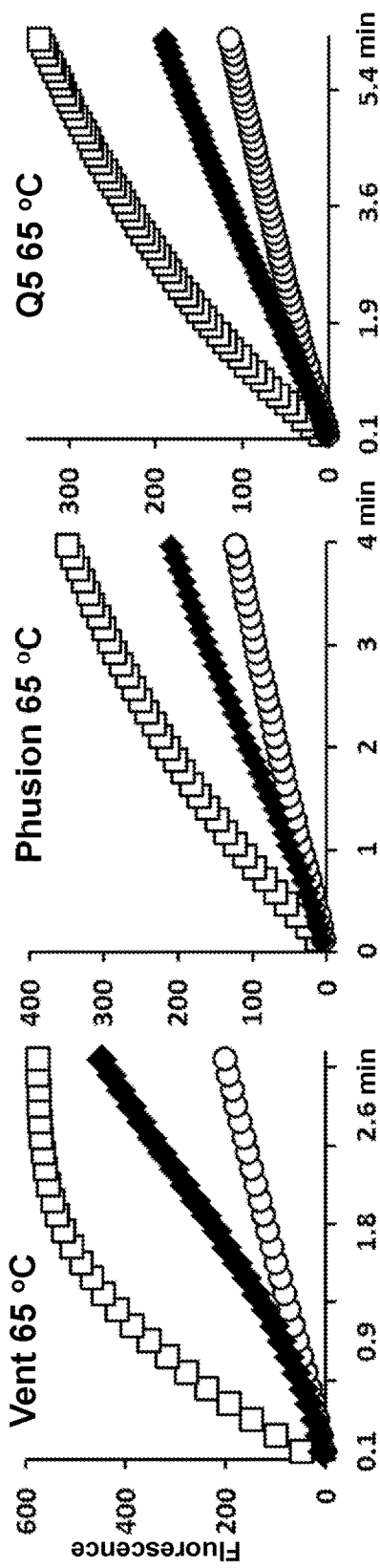
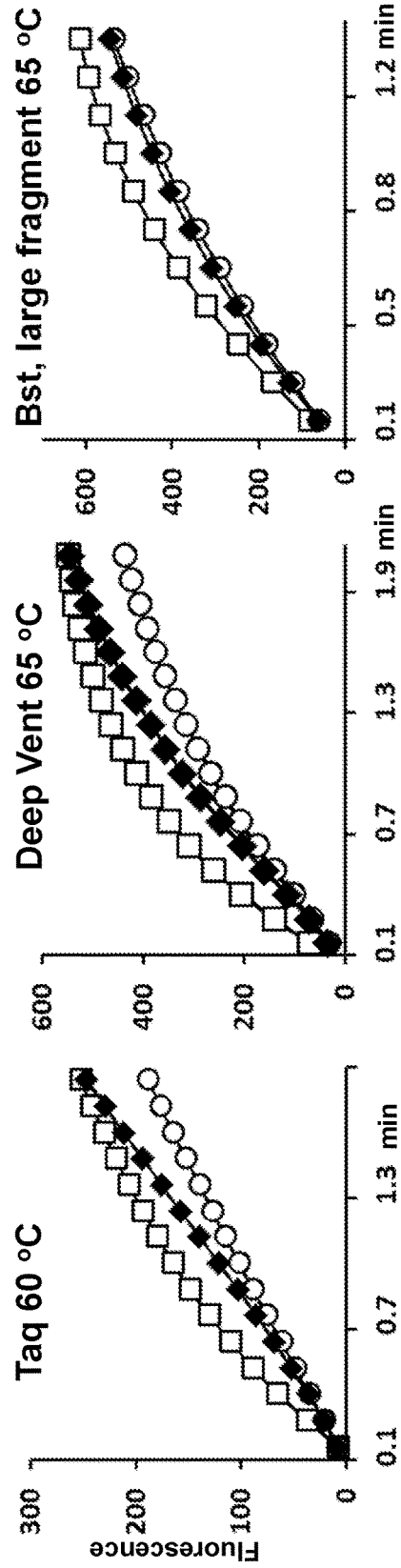

SEQUENCE LISTING

```
<160> NUMBER OF SEQ ID NOS: 23

<210> SEQ ID NO 1
<211> LENGTH: 21
<212> TYPE: DNA
<213> ORGANISM: Artificial Sequence
<220> FEATURE:
<223> OTHER INFORMATION: forward primer

<400> SEQUENCE: 1
gcattcctga agctgacagc a                                             21

<210> SEQ ID NO 2
<211> LENGTH: 24
<212> TYPE: DNA
<213> ORGANISM: Artificial Sequence
<220> FEATURE:
<223> OTHER INFORMATION: reverse primer

<400> SEQUENCE: 2
ctccaggcca gaaagagaga gtag                                          24

<210> SEQ ID NO 3
<211> LENGTH: 22
<212> TYPE: DNA
<213> ORGANISM: Artificial Sequence
<220> FEATURE:
<223> OTHER INFORMATION: oligonucleotide probe sequence
<220> FEATURE:
<221> NAME/KEY: misc_feature
<222> LOCATION: (1)...(1)
<223> OTHER INFORMATION: 5'-FAM-labelled FRET prob
<220> FEATURE:
<221> NAME/KEY: misc_feature
<222> LOCATION: (22)...(22)
<223> OTHER INFORMATION: 3'-BHQ1-labelled FRET probe

<400> SEQUENCE: 3
```

```
ccgtggcctt agctgtgctc gc                                              22
```

```
<210> SEQ ID NO 4
<211> LENGTH: 91
<212> TYPE: DNA
<213> ORGANISM: Artificial Sequence
<220> FEATURE:
<223> OTHER INFORMATION: Human _2-microglobulin target sequence

<400> SEQUENCE: 4
ggcattcctg aagctgacag cattcgggcc gagatgtctc gctccgtggc cttagctgtg     60
ctcgcgctac tctctctttc tggcctggag g                                    91

<210> SEQ ID NO 5
<211> LENGTH: 47
<212> TYPE: DNA
<213> ORGANISM: Artificial Sequence
<220> FEATURE:
<223> OTHER INFORMATION: hairpin loop oligonucleotide aptamer sequence

<400> SEQUENCE: 5
tgcgcgattt aaagcgattc ttagcgtttt cgctttaaat cgcgcat                   47

<210> SEQ ID NO 6
<211> LENGTH: 47
<212> TYPE: DNA
<213> ORGANISM: Artificial Sequence
<220> FEATURE:
<223> OTHER INFORMATION: hairpin loop oligonucleotide aptamer sequence
<220> FEATURE:
<221> NAME/KEY: misc_feature
<222> LOCATION: (18)...(18)
<223> OTHER INFORMATION: U at position 18

<400> SEQUENCE: 6
tgcgcgattt aaagcgautc ttagcgtttt cgctttaaat cgcgcat                   47

<210> SEQ ID NO 7
<211> LENGTH: 47
<212> TYPE: DNA
<213> ORGANISM: Artificial Sequence
<220> FEATURE:
<223> OTHER INFORMATION: hairpin loop oligonucleotide aptamer sequence
<220> FEATURE:
<221> NAME/KEY: misc_feature
<222> LOCATION: (19)...(19)
<223> OTHER INFORMATION: TGCGCGATTTAAAGCGATUCU at position 19

<400> SEQUENCE: 7
tgcgcgattt aaagcgatuc ttagcgtttt cgctttaaat cgcgcat                   47

<210> SEQ ID NO 8
<211> LENGTH: 47
<212> TYPE: DNA
<213> ORGANISM: Artificial Sequence
<220> FEATURE:
<223> OTHER INFORMATION: hairpin loop oligonucleotide aptamer sequence
<220> FEATURE:
<221> NAME/KEY: misc_feature
<222> LOCATION: (21)...(21)
<223> OTHER INFORMATION: U at position 21

<400> SEQUENCE: 8
tgcgcgattt aaagcgattc utagcgtttt cgctttaaat cgcgcat                   47

<210> SEQ ID NO 9
<211> LENGTH: 47
```

```
<212> TYPE: DNA
<213> ORGANISM: Artificial Sequence
<220> FEATURE:
<223> OTHER INFORMATION: hairpin loop oligonucleotide aptamer sequence
<220> FEATURE:
<221> NAME/KEY: misc_feature
<222> LOCATION: (22)...(22)
<223> OTHER INFORMATION: U at position 22

<400> SEQUENCE: 9
tgcgcgattt aaagcgattc tuagcgtttt cgctttaaat cgcgcat                47

<210> SEQ ID NO 10
<211> LENGTH: 47
<212> TYPE: DNA
<213> ORGANISM: Artificial Sequence
<220> FEATURE:
<223> OTHER INFORMATION: hairpin loop oligonucleotide aptamer sequence
<220> FEATURE:
<221> NAME/KEY: misc_feature
<222> LOCATION: (27)...(27)
<223> OTHER INFORMATION: U at position 27

<400> SEQUENCE: 10
tgcgcgattt aaagcgattc ttagcguttt cgctttaaat cgcgcat                47

<210> SEQ ID NO 11
<211> LENGTH: 47
<212> TYPE: DNA
<213> ORGANISM: Artificial Sequence
<220> FEATURE:
<223> OTHER INFORMATION: hairpin loop oligonucleotide aptamer sequence
<220> FEATURE:
<221> NAME/KEY: misc_feature
<222> LOCATION: (28)...(28)
<223> OTHER INFORMATION: U at position 28

<400> SEQUENCE: 11
tgcgcgattt aaagcgattc ttagcgtutt cgctttaaat cgcgcat                47

<210> SEQ ID NO 12
<211> LENGTH: 47
<212> TYPE: DNA
<213> ORGANISM: Artificial Sequence
<220> FEATURE:
<223> OTHER INFORMATION: hairpin loop oligonucleotide aptamer sequence
<220> FEATURE:
<221> NAME/KEY: misc_feature
<222> LOCATION: (29)...(29)
<223> OTHER INFORMATION: U at position 29

<400> SEQUENCE: 12
tgcgcgattt aaagcgattc ttagcgttut cgctttaaat cgcgcat                47

<210> SEQ ID NO 13
<211> LENGTH: 43
<212> TYPE: DNA
<213> ORGANISM: Artificial Sequence
<220> FEATURE:
<223> OTHER INFORMATION: circular hairpin oliigonucleotide aptamer
      sequence

<400> SEQUENCE: 13
aaattatatt cttagcgttt tataatttta aaacgaagtt tta                    43

<210> SEQ ID NO 14
<211> LENGTH: 43
<212> TYPE: DNA
<213> ORGANISM: Artificial Sequence
```

-continued

```
<220> FEATURE:
<223> OTHER INFORMATION: circular hairpin oliigonucleotide aptamer
      sequence
<220> FEATURE:
<221> NAME/KEY: misc_feature
<222> LOCATION: (9)...(9)
<223> OTHER INFORMATION: U at position 9

<400> SEQUENCE: 14
aaattataut cttagcgttt tataatttta aaacgaagtt tta                    43

<210> SEQ ID NO 15
<211> LENGTH: 43
<212> TYPE: DNA
<213> ORGANISM: Artificial Sequence
<220> FEATURE:
<223> OTHER INFORMATION: circular hairpin oliigonucleotide aptamer
      sequence
<220> FEATURE:
<221> NAME/KEY: misc_feature
<222> LOCATION: (10)...(10)
<223> OTHER INFORMATION: U at position 10

<400> SEQUENCE: 15
aaattatatu cttagcgttt tataatttta aaacgaagtt tta                    43

<210> SEQ ID NO 16
<211> LENGTH: 43
<212> TYPE: DNA
<213> ORGANISM: Artificial Sequence
<220> FEATURE:
<223> OTHER INFORMATION: circular hairpin oliigonucleotide aptamer
      sequence
<220> FEATURE:
<221> NAME/KEY: misc_feature
<222> LOCATION: (12)...(12)
<223> OTHER INFORMATION: U at position 12

<400> SEQUENCE: 16
aaattatatt cutagcgttt tataatttta aaacgaagtt tta                    43

<210> SEQ ID NO 17
<211> LENGTH: 43
<212> TYPE: DNA
<213> ORGANISM: Artificial Sequence
<220> FEATURE:
<223> OTHER INFORMATION: circular hairpin oliigonucleotide aptamer
      sequence
<220> FEATURE:
<221> NAME/KEY: misc_feature
<222> LOCATION: (13)...(13)
<223> OTHER INFORMATION: U at position 13

<400> SEQUENCE: 17
aaattatatt ctuagcgttt tataatttta aaacgaagtt tta                    43

<210> SEQ ID NO 18
<211> LENGTH: 43
<212> TYPE: DNA
<213> ORGANISM: Artificial Sequence
<220> FEATURE:
<223> OTHER INFORMATION: circular hairpin oliigonucleotide aptamer
      sequence
<220> FEATURE:
<221> NAME/KEY: misc_feature
<222> LOCATION: (18)...(18)
<223> OTHER INFORMATION: U at position 18

<400> SEQUENCE: 18
aaattatatt cttagcgutt tataatttta aaacgaagtt tta                    43
```

```
<210> SEQ ID NO 19
<211> LENGTH: 43
<212> TYPE: DNA
<213> ORGANISM: Artificial Sequence
<220> FEATURE:
<223> OTHER INFORMATION: circular hairpin oliigonucleotide aptamer
      sequence
<220> FEATURE:
<221> NAME/KEY: misc_feature
<222> LOCATION: (19)...(19)
<223> OTHER INFORMATION: U at position 19

<400> SEQUENCE: 19
aaattatatt cttagcgtut tataattttta aaacgaagtt tta                    43

<210> SEQ ID NO 20
<211> LENGTH: 43
<212> TYPE: DNA
<213> ORGANISM: Artificial Sequence
<220> FEATURE:
<223> OTHER INFORMATION: circular hairpin oliigonucleotide aptamer
      sequence
<220> FEATURE:
<221> NAME/KEY: misc_feature
<222> LOCATION: (20)...(20)
<223> OTHER INFORMATION: U at position 20

<400> SEQUENCE: 20
aaattatatt cttagcgttu tataattttta aaacgaagtt tta                    43

<210> SEQ ID NO 21
<211> LENGTH: 39
<212> TYPE: DNA
<213> ORGANISM: Artificial Sequence
<220> FEATURE:
<223> OTHER INFORMATION: oligonucleotide probe sequence
<220> FEATURE:
<221> NAME/KEY: misc_feature
<222> LOCATION: (37)...(37)
<223> OTHER INFORMATION: FAM-labelled at position 37

<400> SEQUENCE: 21
tttttttttt tttttttttt gcagggccga aggcccugc                          39

<210> SEQ ID NO 22
<211> LENGTH: 59
<212> TYPE: DNA
<213> ORGANISM: Artificial Sequence
<220> FEATURE:
<223> OTHER INFORMATION: oligonucleotide probe sequence
<220> FEATURE:
<221> NAME/KEY: misc_feature
<222> LOCATION: (37)...(37)
<223> OTHER INFORMATION: FAM-labelled at position 37

<400> SEQUENCE: 22
tttttttttt tttttttttt gcagggccga aggcccugca aaaaaaaaa aaaaaaaa      59

<210> SEQ ID NO 23
<211> LENGTH: 12
<212> TYPE: DNA
<213> ORGANISM: Artificial Sequence
<220> FEATURE:
<223> OTHER INFORMATION: hairpin loop oligonucleotide sequence

<400> SEQUENCE: 23
ttcttagcgt tt                                                       12
```

US 10,724,017 B1

INHIBITION OF DNA POLYMERASES BY URACIL-DNA GLYCOSYLASE-CLEAVABLE OLIGONUCLEOTIDE LIGANDS

CROSS-REFERENCE TO RELATED APPLICATION

This application claims the benefit of U.S. Provisional Patent Application No. 62/595,547, filed Dec. 6, 2017, the disclosure of which is herein incorporated by reference in its entirety.

INCORPORATION OF SEQUENCE LISTING

The contents of the text file named "0102384-003US0 Sequence Listing.txt," which was created on Dec. 5, 2017, and is 7 KB in size, are hereby incorporated by reference in their entirety.

BACKGROUND

Aspects of the present invention relate generally to improved methods of blocking DNA polymerase activity with oligonucleotide aptamers at low reaction temperatures, and restoring the enzyme activity upon raising the reaction temperature (e.g., hot-start methods).

DNA polymerases are enzymes used for synthesis of DNA strands by primer extension, wherein the polymerase-catalyzed DNA synthesis may be initiated by oligonucleotide primers hybridized to a complementary template DNA. Initiating DNA synthesis from this template-hybridized primer, DNA polymerases create complementary DNA strands in the presence of corresponding nucleotide 5'-triphosphates. Sequence specificity of nucleotide polymerization, when the oligonucleotide primers bind exclusively to the desired sites and nowhere else, is an important requirement in many applications wherein DNA synthesis is used. However, the efficiency and fidelity of DNA synthesis can be reduced when primers hybridize to non-complementary DNAs, leading to synthesis of incorrect DNA sequences.

Many so-called 'Hot Start' methods have been developed to avoid incorrect primer extension products (e.g., see Paul, N., et al. (2010), for review). One of the most common techniques is based on use of oligonucleotide aptamers (Jayasena S. D., 1999). Aptamers offer a number of advantages over other reported methods. Using a method of molecular evolution (SELEX), they can be quickly engineered in a test tube and then readily and inexpensively manufactured by chemical synthesis. Ideally, an aptamer should: (i) completely block DNA polymerase at low temperatures, and (ii) provide no blockage effect at the desired elevated reaction temperature. Unfortunately, this is very difficult, if not impossible to achieve, and the aptamer structure usually represents a compromise between these two key requirements. New methods, therefore, are needed to improve control of aptamer activity in reaction mixtures containing DNA polymerases.

Particular aspects provide methods for activating an aptamer-inactivated DNA polymerase, comprising: providing a reaction mixture suitable for DNA synthesis, the reaction mixture comprising (i) a DNA polymerase, (ii) a uracil-DNA glycosylase enzymatic activity, and (iii) a DNA polymerase-binding oligonucleotide aptamer that comprises a hairpin structure having a stem sequence portion and a loop sequence portion, wherein the loop sequence portion comprises one or more deoxyuridine nucleotide(s) modifiable by the uracil-DNA glycosylase enzymatic activity, and the aptamer is present in an amount sufficient to inhibit DNA synthesis activity of the DNA polymerase in the reaction mixture; and modifying the aptamer by the uracil-DNA glycosylase enzymatic activity to form a modified aptamer having less or no inhibitory effect on the DNA polymerase, thereby activating or enhancing the DNA synthesis activity of the DNA polymerase, to start and/or increase DNA synthesis in the reaction mixture. In the methods, for example, modifying the aptamer may be facilitated by use of a reaction temperature that facilitates the DNA polymerase activity and/or the uracil-DNA glycosylase enzymatic activity. In the methods, modifying the aptamer may be facilitated by increasing the temperature of the reaction mixture from a first temperature to a second temperature that activates or more strongly facilitates the uracil-DNA glycosylase enzymatic activity. In the methods, providing the reaction mixture may comprise dissolving a dried form of at least one of the (i) DNA polymerase, (ii) oligonucleotide aptamer, and (iii) uracil-DNA glycosylase enzymatic activity, into an aqueous solution. In the methods, the DNA synthesis may result in DNA amplification in the reaction mixture (e.g., wherein the DNA amplification is an isothermal amplification reaction, and/or wherein the DNA amplification is PCR). The methods may comprise detecting a presence of a target DNA in the reaction mixture, and/or measuring an amount of a target DNA in the reaction mixture. In the methods, the oligonucleotide aptamer may be circular. In the methods, the uracil-DNA glycosylase enzymatic activity may be effective to modify the oligonucleotide aptamer by generating at least one abasic site within the loop sequence portion thereof. In the methods, the uracil-DNA glycosylase may be or comprise Afu Uracil-DNA Glycosylase. In the methods, the loop sequence portion may be or comprise a nucleotide sequence 5'-TTCTTAGCGTTT-3' (SEQ ID NO:23) wherein one or more thymidine nucleotides at positions 1, 2, 10, 11, and 12 of the SEQ ID NO:23 sequence are substituted by one or more deoxyuridine nucleotides.

Additional aspects provide kits for activating an aptamer-inactivated DNA polymerase, comprising: a uracil-DNA glycosylase enzymatic activity; and a DNA polymerase-binding oligonucleotide aptamer sequence that is capable of forming a hairpin structure having a stem sequence portion and a loop sequence portion, wherein the loop sequence portion comprises one or more deoxyuridine nucleotides modifiable by the uracil-DNA glycosylase enzymatic activity. In the kits, the loop sequence portion may be or comprise a nucleotide sequence 5'-TTCTTAGCGTTT-3' (SEQ ID NO:23) wherein one or more thymidine nucleotides at positions 1, 2, 10, 11, and 12 of the SEQ ID NO:23 sequence are substituted by one or more deoxyuridine nucleotides. In the kits, the oligonucleotide aptamer may be a circular molecule. In the kits, the uracil-DNA glycosylase enzymatic activity may be effective to modify the oligonucleotide aptamer by generating at least one abasic site within the loop sequence portion. In the kits, the uracil-DNA glycosylase may be or comprise Afu Uracil-DNA Glycosylase.

Further aspects provide reaction mixtures for use in a method of DNA synthesis, which reaction mixture comprises: (i) a DNA polymerase, and (ii) a DNA polymerase-binding oligonucleotide aptamer that comprises a hairpin structure having a stem sequence portion and a loop sequence portion, wherein the loop sequence portion comprises one or more deoxyuridine nucleotides modifiable by a uracil-DNA glycosylase enzymatic activity, and the aptamer is present in an amount sufficient to inhibit DNA synthesis activity of the DNA polymerase in the reaction mixture. The reaction mixtures may further comprise (iii) a uracil-DNA glycosylase enzymatic activity sufficient, under suitable conditions, to modify the oligonucleotide aptamer to reduce or eliminate binding of the oligonucleotide aptamer to the DNA polymerase, thereby activating or enhancing the DNA synthesis activity of the DNA polymerase. In the reaction mixtures, at least one of the DNA polymerase activity and/or the uracil-DNA glycosylase enzymatic activity may be temperature dependent. In the reaction mixtures, the uracil-DNA glycosylase enzymatic activity may increase with increasing temperature of the reaction mixture from a first temperature to a second temperature that activates or more strongly facilitates the uracil-DNA glycosylase enzymatic activity. In the reaction mixtures, the DNA polymerase, and/or oligonucleotide aptamer, and/or uracil-DNA glycosylase enzymatic activity may be present in the reaction mixture in a dried state. In the reaction mixtures, the loop sequence portion may be or comprise a nucleotide sequence 5'-TTCTTAGCGTFT-3' (SEQ ID NO:23) wherein one or more thymidine nucleotides at positions 1, 2, 10, 11, and 12 of the SEQ ID NO:23 sequence are substituted by one or more deoxyuridine nucleotides. In the reaction mixtures, the oligonucleotide aptamer may be a circular molecule. In the reaction mixtures, the uracil-DNA glycosylase enzymatic activity may be effective to modify the oligonucleotide aptamer by generating at least one abasic site within the loop sequence portion. In the reaction mixtures, the uracil-DNA glycosylase may be or comprise Afu Uracil-DNA Glycosylase. The reaction mixtures may further comprise one or more of dATP, dCTP, dGTP, and/or dTTP, and/or $Mg^{2+}$ ion.

Yet further aspects provide an oligonucleotide aptamer, comprising a DNA polymerase-binding nucleic acid sequence that is capable of forming a hairpin structure having a stem sequence portion and a loop sequence portion, wherein the loop sequence portion is or comprises a nucleotide sequence 5'-TTCTTAGCGTTT-3' (SEQ ID NO:23), wherein one or more thymidine nucleotides at positions 1, 2, 10, 11, and 12 of the SEQ ID NO:23 sequence are substituted by one or more deoxyuridine nucleotides modifiable by a uracil-DNA glycosylase enzymatic activity (e.g., by Afu Uracil-DNA Glycosylase). The oligonucleotide aptamers may be circular molecules. The circular oligonucleotide aptamers may comprises a duplex stem sequence portion positioned between two loop sequence portions. In the circular oligonucleotide aptamers comprising a duplex stem sequence portion positioned between two loop sequence portions, the two loop sequence portions may be the same or different sequences. The oligonucleotide aptamers may be in combination with a DNA polymerase.

BRIEF DESCRIPTION OF THE DRAWINGS

FIG. 2 shows, according to particular exemplary aspects, structures of noncircular stem-loop deoxyribonucleotide aptamers used in exemplary working Examples of the invention with uracil-DNA glycosylase (FIGS. 3A, 3B, and 7A-F). The symbol "U" is deoxyribouridine nucleotide. Aptamers SEQ ID NOS:6-12 are the structural analogs of unmodified aptamer SEQ ID NO:5 incorporating deoxyuridine at various positions within the loop sequence.

FIG. 4 shows, according to particular exemplary aspects, structures of eight additional circular stem-loop deoxyribonucleotide aptamers SEQ ID NOS:13-20 (right column). The central column shows linear oligonucleotide sequences used to prepare the corresponding circular aptamers SEQ ID NOS:13-20 (right column) as described herein in Example 2. The symbol "p" indicates a 5'-phosphate moiety. Circular stem-loop deoxyribonucleotide aptamers SEQ ID NOS: 14-20 are structural homologs of the unmodified circular aptamer SEQ ID NO: 13 representing all possible (seven), single deoxythymidine-to-deoxyuridine substitutions (marked by symbol "U") within the loop sequence as indicated. These aptamers were used in the 5'-nuclease PCR assays of FIGS. 5A and 5B.

FIGS. 7A through 7F show, according to particular exemplary aspects, uracil-DNA glycosylase-induced activation of Taq (FIG. 7D), Phusion® (FIG. 7B), Q5® (FIG. 7C), Vent® (FIG. 7A), Deep Vent® (FIG. 7E) and Bst large fragment (FIG. 7F) DNA polymerases that were initially deactivated (i.e., "inhibited" or "blocked") by the presence of aptamer SEQ ID NO:12 (♦ curves). FIGS. 7A through 7F also show the change of fluorescence with time in the absence of uracil-DNA glycosylase for the aptamer-blocked (○) and unblocked (□) DNA polymerase. The DNA polymerase activity was monitored by extension of the self-priming hairpin-like fluorescent probe SEQ ID NO:21 (see FIG. 6), which was present in the reaction mixture with all four dNTPs in a magnesium-containing buffer. In all cases, experiments were performed at 60 or 65° C., as indicated in each Figure. The structure of aptamer SEQ ID NO: 12 is shown in FIG. 2, and details of the experimental setup, results analysis and conclusions are provided below in "Example 4."

DETAILED DESCRIPTION

Definitions

Figure 1:
FIG. 1 shows, according to particular exemplary aspects, a portion of a human β2-microglobulin gene sequence (SEQ ID NO:4), forward and reverse primers (SEQ ID NOS: 1-2, respectively) and a 22-mer fluorescent probe (SEQ ID NO:3), which were used in exemplary 5'-nuclease PCR assays of the present invention from which exemplary results are shown in FIGS. 3 and 5. The primers and probe are shown aligned with an amplified human β2-microglobulin fragment sequence in 5'→3' orientation as indicated.

Terms and symbols of biochemistry, nucleic acid chemistry, molecular biology and molecular genetics used herein follow those of standard treatises and texts in the field (e.g., Sambrook, J., et al., 1989; Kornberg, A. and Baker, T., 1992: Gait, M. J., ed., 1984; Lehninger, A. L., 1975; Eckstein, F., ed., 1991, and the like). To facilitate understanding of particular exemplary aspects of the invention, a number of terms are discussed below.

In particular aspects, "aptamer" or "oligonucleotide aptamer" refers herein to an oligonucleotide that can form a secondary structure such as hairpin or stem-loop structure that is capable of binding to a DNA polymerase and blocking its DNA synthesis enzymatic activity. Examples of such aptamers and methods of their sequence selection (design) can be found, for instance, in Yakimovich, O. Yu., et al. (2003); Jayasena, S. D. (1999): U.S. Pat. No. 5,693,502 to Gold, L. and Jayasena. S. D., which are incorporated here by reference. The phrase "aptamer, that binds to the DNA polymerase, in an amount sufficient to inhibit DNA synthesis activity of the DNA polymerase," as used herein, means that the DNA synthesis activity of the DNA polymerase is at least partially inhibited (e.g., inhibited to a level in the range of from about 1% to about 99.99%). Any level of aptamer inhibition of the DNA synthesis activity of the DNA polymerase can provide an advantage for DNA synthesis, and thus according to particular preferred hot start aspects of the present invention, the DNA synthesis activity of the DNA polymerase is substantially inhibited (e.g., inhibited to a level in the range of about 80% to 99.99%, or to any subrange or level therein), or completely (100%) inhibited, providing an advantage over other 'hot start' technologies (e.g., Paul N. et al, 2010). Likewise, in the disclosed methods, "modifying the aptamer by a uracil-DNA glycosylase enzymatic activity to reduce or eliminate the binding of the oligonucleotide aptamer to the DNA polymerase and activate the DNA synthesis activity of the DNA polymerase" is preferably complete (100%) or substantially complete (e.g., inhibited to a level in the range of about 80% to 99.99%, or to any subrange or level therein), but can be partial (e.g., inhibited to a level in the range of from about 1% to about 99.99%), as exemplified herein (e.g., FIGS. 3, 5, and 7).

An oligonucleotide aptamer may comprise ribo- or 2'-deoxyribonucleotides or a combination thereof. Oligonucleotide aptamers may be modified. Regarding the aptamers, the term "modification" is used herein in two different aspects, wherein the aptamers can be (i) modified synthetically, e.g., during the oligonucleotide synthesis, and (ii) enzymatically-modified in the context of or during DNA synthesis reactions. Synthetically, the aptamers may incorporate any kind and/or number of structural modifications across the length of the aptamer (e.g., in the middle or at the ends of the oligonucleotide chain). The term "structural modifications" refers to any chemical substances such as atoms, moieties, residues, polymers, linkers or nucleotide analogs, etc., which are usually of a synthetic nature and which are not commonly present in naturally-occurring nucleic acids. As used herein, the term "structural modifications" also include nucleoside or nucleotide analogs which are rarely present in naturally-occurring nucleic acids including but not limited to inosine (hypoxanthine), 5-bromouracil, 5-methylcytosine, 5-iodouracil, 2-aminoadenosine, 6-methyladenosine, pseudouridine, deoxyuridine, and the like. The structural modifications can be "duplex-stabilizing modifications." "Duplex-stabilizing modifications" refer to structural modifications, the presence of which in double-stranded nucleic acids provides a duplex-stabilizing effect when compared in thermal stability, usually measured as "Tm." with respective nucleic acid complexes that have no such structural modification and, e.g., comprise natural nucleotides. Duplex-stabilizing modifications are structural modifications that are most commonly applied in synthesis of probes and primers, as represented by modified nucleotides and 'tails' like intercalators and minor groove binders as, for example, disclosed in U.S. Pat. No. 8,349,556 to Kutvavin, I. V.; U.S. Pat. No. 7,794,945 to Hedgpeth, J., et al.; U.S. Pat. No. 6,127,121 to Meyer, Jr., R. B., et al.; U.S. Pat. No. 5,801,155 to Kutyavin, I. V., et al., and the references cited in. Duplex-stabilizing modifications can be used to prepare aptamers of the invention, for example, to improve thermal stability of stem (duplex) structures of hairpin-like aptamers. In preferred methods of the invention, the oligonucleotide aptamers are modified in (e.g., during) the DNA synthesis reactions using enzymatic activity of one or more uracil-DNA glycosylase(s). In this aspect, the terms "modify," "modification." and "structural modifications" mean changes in the original synthetic structure of the aptamers. The change is triggered by a uracil-DNA glycosylase activity, resulting in removal of one or more uracil bases to produce respective abasic site(s). In the methods of the invention, these uracil-DNA glycosylase-triggered structural modifications reduce or eliminate the ability of the oligonucleotide aptamer to bind to the DNA polymerase and block or reduce its activity in the reaction mixture. In particular embodiments, the hairpin-like aptamers incorporate deoxyuridine nucleotides within the loop sequence thereof. The hairpin-like aptamers of the invention can be circular molecules.

In particular aspects, the term "secondary structure" refers to an intramolecular complex formation of one sequence in a poly- or oligonucleotide with another sequence in the same polymer due to complete or partial complementarity between these two sequences formed based on the principal rules of Watson-Crick base pairing. The terms "hairpin" structure or "stem-loop" structure as referred to herein describe elements of secondary structure, and both terms refer to a double-helical region (stem) formed by base pairing between complementary sequences within a single strand RNA or DNA.

As used herein, the term "uracil-DNA glycosylases" refer to enzymes that remove uracil bases or uracil base analogs while leaving the sugar-phosphate backbone intact, creating an apurinic/apyrimidinic site, commonly referred herein to as an "abasic site." The term "DNA polymerase" refers to an enzyme that catalyzes synthesis of deoxyribonucleic acids (DNAs), most commonly double-stranded DNAs, using single-stranded DNAs as "templates." The DNA synthesis is usually initiated by an oligonucleotide primer that is hybridized to a template strand.

Starting from this template-hybridized primer, DNA polymerase creates a Watson-Crick complementary strand in the presence of 2'-deoxyribonucleotide 5'-triphosphates (dNTPs). The term "DNA polymerase," as used herein, also incorporates "reverse transcriptases," enzymes which can perform DNA synthesis using single-stranded ribonucleic acids (RNAs) as template strands.

"Polynucleotide" and "oligonucleotide" are used herein interchangeably and in each case means a linear polymer of nucleotide monomers. Polynucleotides typically range in size from a few monomeric units, e.g., 5-60, when they are usually referred to as "oligonucleotides," to several thousand monomeric units. The exact size will depend on many factors, which in turn depends on the ultimate function or use of the oligonucleotide. The oligonucleotides may be generated in any manner, including chemical synthesis, DNA replication, reverse transcription, or a combination thereof. Unless otherwise specified, whenever a polynucleotide or oligonucleotide is represented by a sequence of letters, for example, 5'-TTCTTAGCGTTT-3' (SEQ ID NO:23), it is understood herein, unless otherwise specified in the text, that the nucleotides are in 5'-3' order from left to right and that "A" denotes deoxyadenosine. "C" denotes deoxycytidine, "G" denotes deoxyguanosine, and "T" denotes deoxythymidine. Usually DNA polynucleotides comprise these four deoxyribonucleosides linked by phosphodiester linkage whereas RNA comprises uridine ("U") in place of "T" for the ribose counterparts.

The terms "oligonucleotide primer" and/or "primer" refer to a single-stranded DNA or RNA molecule that hybridizes to a target nucleic acid and serves to prime enzymatic synthesis of a second nucleic acid strand in the presence of a DNA polymerase. In this case, the target nucleic acid "serves as a template" for the oligonucleotide primer.

In particular aspects, the terms "complementary" or "complementarity" are used herein in reference to the polynucleotide base-pairing rules. Double-stranded DNA, for example, consists of base pairs wherein, for example, G complexes or pairs with C via formation of a three hydrogen bond complex, and A complexes or pairs with T via formation of a two hydrogen bond complex, such that G is regarded as being complementary to C. and A is regarded as being complementary to T. In this sense, for example, an oligonucleotide 5'-GATTTC-3' is complementary to the sequence 3'-CTAAAG-5' via intrastrand G:C and A:T hydrogen bonding interactions. Complementarity may be "partial" or "complete." In partial complementarity, only some of the nucleic acids bases are matched according to the base pairing rules. The terms may also be used in reference to individual nucleotides and oligonucleotide sequences within the context of polynucleotides (e.g., inter-strand complementarity). The terms "complementary" or "complementarity" refer to the most common type of complementarity in nucleic acids, namely Watson-Crick base pairing as described above, although the oligonucleotides may alternately participate in other types of "non-canonical" pairings like Hoogsteen, wobble and G-T mismatch pairing.

The terms "natural nucleosides," refers to the art-recognized four 2'-deoxyribonucleosides (usually named herein as "deoxynucleosides" or "deoxyribonucleosides") that are found in DNAs isolated from natural sources. Natural nucleosides are deoxyadenosine, deoxycytidine, deoxyguanosine, and deoxythymidine. The term also encompasses their ribose counterparts, with uridine (U) in place of thymidine. The same name variations are applied herein to "natural nucleotides."

As used herein, the terms "unnatural nucleosides" or "modified nucleosides" refer to nucleoside analogs that are different in their structure from those natural nucleosides for DNA and RNA polymers. Some naturally occurring nucleic acids contain nucleosides that are structurally different from the natural nucleosides defined above, for example, DNAs of eukaryotes may incorporate 5-methyl-cytosine, and tRNAs contain many nucleoside analogs. However, as used herein, the terms "unnatural nucleosides" or "modified nucleosides" encompasses these nucleoside modifications even though they can be found in natural sources. For example, ribothymidine as well as deoxyuridine are examples of unnatural nucleotides referred to herein.

The term "reaction mixture" generally means herein a solution containing all the necessary reactants for performing DNA synthesis such as a DNA polymerase, oligonucleotide primer(s), template polynucleotide, deoxyribonucleoside 5'-triphosphates, reaction cofactors (e.g., magnesium or manganese ions), etc. The reaction mixture can incorporate other reaction components that help to improve the DNA synthesis (e.g., buffering and salt components, detergents, proteins like bovine serum albumin (BSA), scavengers, etc.) or components that are necessary for detection of the newly synthesized DNA molecules such as, for example, fluorescent dyes and oligonucleotide probes. A reaction mixture is usually prepared at low temperatures at which enzymatic components are inactive, for example, by mixing the components on ice at ~0° C. When the reactions are ready, the mixtures can be heated to the desired reaction temperatures. In this aspect, the term "reaction temperature" refers to a temperature or a temperature range at which DNA synthesis is performed. In case of PCR reactions, it is usually taken as the lowest thermo-cycling temperature, commonly called the annealing temperature.

The symbol "dNTPs" is an abbreviation of a mixture of all four natural deoxynucleoside 5'-triphosphates that are useful to facilitate primer extension with a DNA polymerase and/or amplification. Respectively, the abbreviations "dATP," "dCTP," "dGTP," and "dTTP" correspond to the individual nucleotides. In some embodiments, the four dNTPs are present at equal concentrations. In other embodiments, the concentrations of the dNTPs are not all identical. In some embodiments, fewer than all four dNTPs are present. For example, only one dNTP may be present, or a pair-wise combination, or three of four dNTPs may be present in the mixture.

In some aspects, "amplification" and "amplifying" deoxyribonucleic acids, in general, refer to a procedure wherein multiple copies of DNA of interest are generated. The DNA amplification can be performed at a constant temperature using "isothermal amplification reactions." Examples of isothermal amplification reactions include, but are not limited to, Strand Displacement Amplification (SDA) (U.S. Pat. No. 5,270,184 to Walker, G. T., et al.; U.S. Pat. No. 6,214,587 to Dattagupta, N., et al.), Rolling Circle amplification (RCA) (U.S. Pat. No. 5,854,033 to Lizardi, P.), Loop-Mediated Amplification (IMA) (U.S. Pat. No. 6,410,278 to Notomi, T. and Hase, T.), isothermal amplification using chimeric or composite RNA/DNA primers (U.S. Pat. No. 5,824,517 to Cleuziat, P. and Mandrand, B.: U.S. Pat. No. 6,251,639 to Kurn, N.), Nucleic Acid Sequence-Based Amplification (NASBA) (U.S. Pat. No. 6,063,603 to Davey, C. and Malek, L. T.), and many other methods.

"PCR" is an abbreviation of "polymerase chain reaction," an art-recognized nucleic acid amplification technology (e.g., U.S. Pat. Nos. 4,683,195 and 4,683,202 to Mullis, K. B.). Commonly used PCR protocol employs two oligonucleotide primers, one for each strand, designed such that extension of one primer provides a template for the other primer in the next PCR cycle. Generally, a PCR reaction consists of repetitions (cycles) of (i) a denaturation step that separates the strands of a double-stranded nucleic acid, followed by (ii) an annealing step, which allows primers to anneal to positions flanking a sequence of interest on a separated strand, and then (iii) an extension step that extends the primers in a 5' to 3' direction, thereby forming a nucleic acid fragment complementary to the target sequence. Each of the above steps may be conducted at a different temperature using an automated thermocycler. The PCR cycles can be repeated as often as desired resulting in an exponential accumulation of a target DNA fragment whose termini are usually defined by the 5'-ends of the primers used. Although conditions of PCR can vary in a broad range, a double-stranded target nucleic acid is usually denatured at a temperature of >90° C., primers are annealed at a temperature in the range of about 50-75° C., and the extension is preferably performed in a 72-75° C. temperature range. In PCR methods, the annealing and extension can be combined into one stage (i.e., using a single temperature). The term "PCR" encompasses its numerous derivatives such as "RT-PCR," "real-time PCR," "nested PCR." "quantitative PCR" "multiplexed PCR," "asymmetric PCR," and the like.

"Real-time detection" means an amplification reaction for which the amount of reaction product, i.e., target nucleic acid, is monitored as the reaction proceeds. Real-time detection is possible when all detection components are available during the amplification and the reaction composition and conditions support both stages of the reaction: the amplification and the detection.

As used herein, the term "kit" refers to any system for delivering materials. In the context of reaction assays, such delivery systems include elements allowing the storage, transport, or delivery of reaction components such as oligonucleotides, buffering components, additives, reaction enhancers, enzymes, and the like in the appropriate containers from one location to another commonly provided with written instructions for performing the assay. Kits may include one or more enclosures or boxes containing the relevant reaction reagents and supporting materials. The kit may comprise two or more separate containers wherein each of those containers includes a portion of the total kit components. The containers may be delivered to the intended recipient together or separately.

In general, the term "design" in the context of the methods has broad meaning and in certain respects is equivalent to the term "selection." For example, the terms "primer design" and "aptamer design" can mean or encompass selection of a particular oligonucleotide structure including the nucleotide primary sequence and structural modifications (e.g., labels, modified nucleotides, linkers, etc.). In particular aspects, the terms "system design" and "assay design" relate to the selection of any, sometimes not necessarily to a particular, methods including all reaction conditions (e.g., temperature, salt, pH, enzymes, including the aptamer-modifying enzymes and DNA polymerase, oligonucleotide component concentrations, etc.), structural parameters (e.g., length and position of primers and probes, design of specialty sequences, etc.), and assay derivative forms (e.g., post-amplification, real time, immobilized, FRET detection schemes, etc.) chosen to amplify and/or to detect the nucleic acids of interest.

Reversible Blocking DNA Synthesis Activity of DNA polymerases Using Oligonucleotide Stem-Loop Aptamers of the Invention.

Prior art applications of oligonucleotide aptamers during DNA synthesis are directed at blocking DNA polymerase, preferably completely, at low temperatures, while releasing the DNA polymerase activity, preferably completely, at an elevated reaction temperature. It is difficult, however, to achieve complete 'block-and-release' formats using conventional aptamer-based methods (e.g., Yakimovich, O. Yu., et al. (2003); Jayasena, S. D. (1999): U.S. Pat. No. 5,693,502 to Gold, L. and Jayasena, S. D. (1997)). Effective blockage of DNA polymerase at low temperatures commonly leads to ineffective release of the enzyme at the elevated reaction temperature and vice versa. Aspects of the present invention provide a solution to this long-standing problem in the art. As in the conventional approaches cited above, the DNA polymerase activity is blocked or reduced in methods of the invention by the presence of an oligonucleotide hairpin-like aptamer that binds to the DNA polymerase, blocking the DNA synthesis activity of the DNA polymerase. Unlike prior art techniques, however, in methods of the invention, the aptamer-inactivated DNA polymerase is activated by providing, to a DNA synthesis reaction mixture, one or more uracil-DNA glycosylases that recognize the oligonucleotide aptamer as a substrate and modify its structure. This structural modification reduces or eliminates the binding of the oligonucleotide aptamer to the DNA polymerase and thereby reactivates the DNA synthesis activity of the DNA polymerase.

In some embodiments of the invention, activation of an aptamer-inactivated DNA polymerase in a reaction mixture, comprising (i) a DNA polymerase, (ii) oligonucleotide aptamer in an amount effective to inhibit the DNA synthesis activity of the DNA polymerase, (iii) uracil-DNA glycosylase(s) and other components necessary for DNA synthesis, is facilitated using a reaction temperature that accelerates (or facilitates) both DNA polymerase and aptamer-modifying enzyme activities. For example, the reaction mixture can be prepared at a low temperature (first temperature) at which a DNA polymerase is effectively blocked by an aptamer and a uracil-DNA glycosylase enzyme has sufficiently reduced or preferably no activity (e.g., at 0° C.), and then the activation of the aptamer-inactivated DNA polymerase is facilitated by heating the reaction to a temperature (second temperature) that accelerates or facilitates the uracil-DNA glycosylase enzymatic activity. If necessary, a DNA polymerase can be activated by the uracil-DNA glycosylase(s) at any temperature below the reaction temperature for DNA synthesis. This approach can be applied, for example, when a particular uracil-DNA glycosylase enzyme is unstable at the reaction temperature for DNA synthesis, for example, due to denaturation. In this case, the DNA polymerase is first activated at an intermediate temperature wherein the uracil-DNA glycosylase is active and then heated to the reaction temperature to perform DNA synthesis.

In some aspects, the reaction mixture is created by addition of aqueous solution to one or more reaction components which are initially in a dried state as disclosed and described, for example, in U.S. Pat. No. 3,721,725 to Briggs, A. R. and Maxwell, T. J. (1973) (incorporated herein by reference). For example, in some methods of the invention for DNA amplification and detection, the aqueous solution can be a sample solution or solution that contains one or more polynucleotide templates for DNA synthesis, whereas all other reaction components, or particular desired reactions components or desired combinations thereof such as the DNA polymerase, aptamer, uracil-DNA glycosylase enzyme(s), dNTPs, catalytic cofactors like magnesium ($Mg^{2+}$) or manganese ($Mn^{2+}$) salt (e.g., chloride salts), buffering components, detergents, proteins like bovine serum albumin (BSA), scavengers, etc., are present in a dry state.

In some aspects, DNA synthesis results in DNA amplification in the reaction mixture. The DNA amplification can be an isothermal amplification reaction, for example, as described in U.S. Pat. No. 5,270,184 to Walker, G. T., et al.; U.S. Pat. No. 6,214,587 to Dattagupta, N., et al.; U.S. Pat. No. 5,854,033 to Lizardi, P.; U.S. Pat. No. 6,410,278 to Notomi, T. and Hase, T.; U.S. Pat. No. 5,824,517 to Cleuziat, P. and Mandrand, B.; U.S. Pat. No. 6,251,639 to Kurn, N.; U.S. Pat. No. 6,063,603 to Davey, C. and Malek, L. T., and many other methods. In other aspects, the DNA amplification can be a PCR reaction (e.g., U.S. Pat. Nos. 4,683,195 and 4,683,202 to Mullis, K. B.). In methods of the invention, the DNA amplification may be performed for detection and/or for measuring an amount of a target DNA in the reaction mixture.

Aptamers of the invention fold into hairpin secondary structures having stem and loop sequence portions, wherein the loop sequence portions contain one or more deoxyuridine nucleotide(s) that can be recognized and removed from the aptamer nucleotide sequence by a uracil-DNA glycosylase enzymatic activity. Relative to unmodified aptamers, the glycosylase-modified aptamers of the invention have reduced or no inhibitory effect on the DNA polymerase, thereby activating or enhancing the DNA synthesis activity of the DNA polymerase, to start and/or increase DNA synthesis in the reaction mixture.

The oligonucleotide aptamers as well as oligonucleotide primers and probes can be prepared by any method of oligonucleotide synthesis described in the art, but preferred is the most modern chemistry based on (2-cyanoethyl)-(N, N-diisopropyl)]-phosphoramidites (Example 1). Respectively protected nucleotides and their numerous derivatives, linkers, dyes, tails, solid supports, and other necessary components can be prepared by methods of organic chemistry or obtained from market providers such as, for example, Glen Research and Biosearch Technologies. Suppliers such as Integrated DNA Technologies and Biosearch Technologies also offer oligonucleotide custom synthesis including numerous structural modifications including deoxyuridine nucleotides. For a particular DNA polymerase in the methods of the invention, selection of an aptamer structure, including one or more deoxyuridine nucleotide(s), their location within the loop sequence, and uracil-DNA glycosylase enzymes, is intended to achieve (i) complete deactivation of the DNA polymerase at the initial reaction assembly temperature, (ii) substantially complete or complete (or as much as possible) deactivation of the DNA polymerase at the elevated reaction temperature for DNA synthesis, and (iii) substantially complete or complete (or as much as possible) activation of this enzyme at the DNA synthesis reaction temperature once the aptamer has been modified by the uracil-DNA glycosylase enzymatic activity. Preferably, the prospective uracil-DNA glycosylases should not interfere with DNA synthesis or DNA amplification. The location and number of deoxyuridines within an aptamer loop sequence, as well as the rate and efficiency of the uracil-DNA glycosylases is taken into consideration. Preference is given to a number of deoxyuridine and/or their locations within an aptamer loop sequence that have little or no negative effect on stability of the aptamer-polymerase complex, but sufficiently disturb structural integrity of the aptamer and its ability to bind to a DNA polymerase after modification by a uracil-DNA glycosylase to provide optimal DNA polymerase activation. Use of deoxyuridine nucleotides within loop segments of noncircular (SEQ ID NOS:6-12) and circular (SEQ ID NOS:14-20) hairpin-like aptamers is illustrated in FIGS. 3 and 5, respectively. Surprisingly, positioning of a single base modification in the loop segments of both noncircular and circular aptamers showed excellent results in a number of exemplary assays herein.

Figures 3A, 3B:
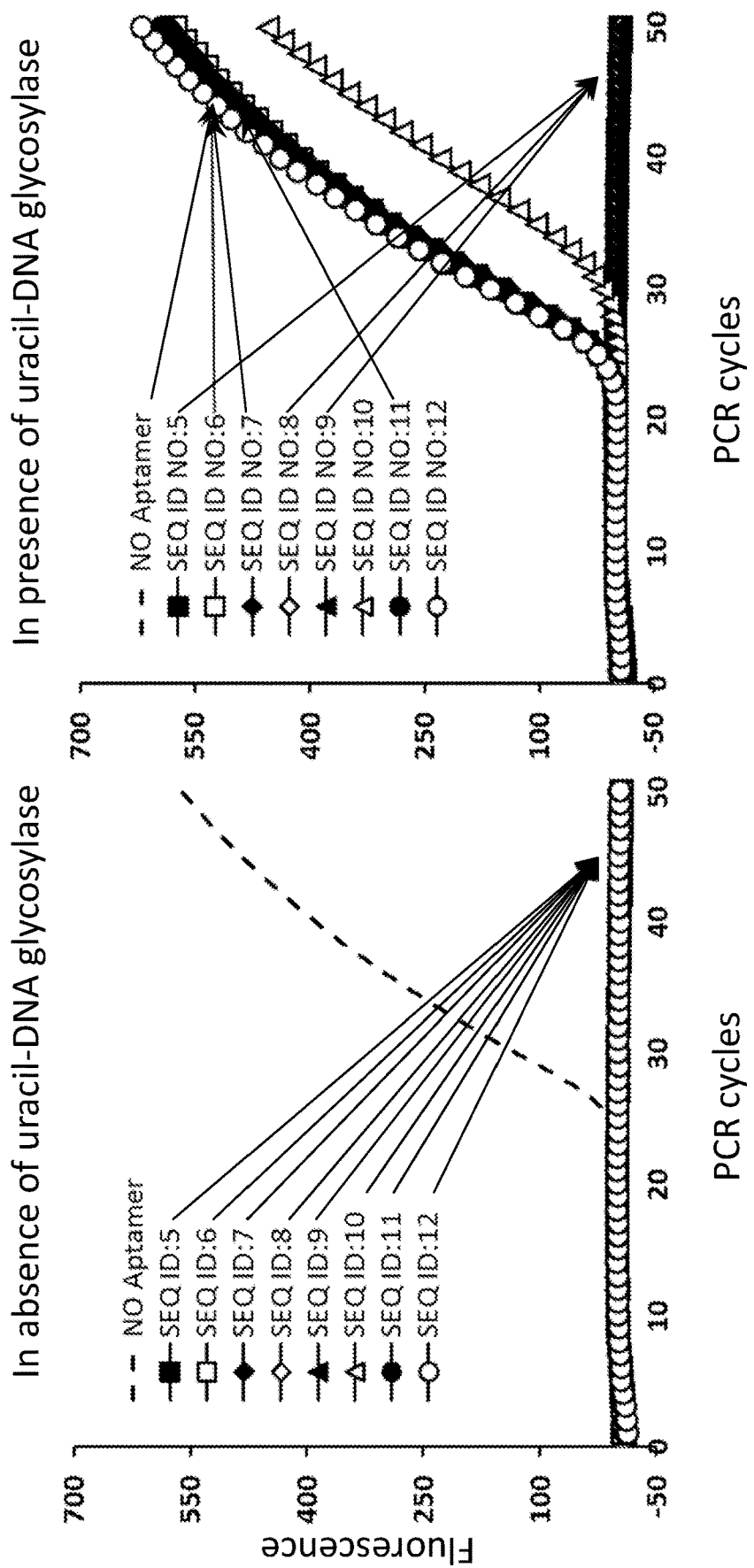
FIGS. 3A and 3B show, according to particular exemplary aspects, the results of fluorescence monitoring of reaction mixtures during PCR (real-time curves) in the presence of the individual aptamers listed in FIG. 2. Sequences of the amplified human β2-microglobulin template, primers and 22-mer FRET probe used in these PCR assays are as shown in FIG. 1. Dashed lines are real-time curves obtained in the absence of any aptamer. Experiments were conducted in the absence (FIG. 3A) or presence (FIG. 3B) of Afu Uracil-DNA Glycosylase. Experimental details are provided below in "Example 3."

According to the prior art (Yakimovich, O. Yu., et al. (2003); Jayasena, S. D. (1999) U.S. Pat. No. 5,693,502 to Gold, L. and Jayasena, S. D.), efficiency of hairpin-type aptamer binding to DNA polymerase is determined by (i) a substantially conservative loop segment sequence, and (ii) the length of the stem duplex, which preferably needs to be at least ~17 base pairs long (Yakimovich, O. Yu., et al. (2003). According to particular aspects disclosed herein, the sequence and the structure of the stem fragment is another important factor affecting the stability of an aptamer-polymerase complex. For example, the 17-base pair long stem sequence of noncircular aptamer SEQ ID NO:5 used in the present working Examples was empirically determined, and comprises a A-T rich duplex surrounded by G-C clamps (see FIG. 2). This aptamer and many of its derivatives (SEQ ID NOS:6-12) were nonetheless effective in blocking not only Taq polymerase, but also many other DNA polymerases (FIGS. 7A-7F). As exemplified herein (FIGS. 5A and 5B), circularization of aptamers (Examples 2 and 3) allowed (i) reduction of the hairpin stem length by 3 base pairs and (ii) use of a relatively unstable A-T-rich sequence in the stem design, while maintaining utility of the aptamers in methods of the invention. Regardless of these changes in the stem design parameters, generally regarded in the prior art as negative/unfavorable changes, unmodified circular aptamer SEQ ID NO:13 (FIG. 4) as well as many of its deoxyuridine-modified derivatives (SEQ ID NOS:14-20) inactivated Taq DNA polymerase in PCR assays (FIG. 5A) as effectively as unmodified noncircular aptamer SEQ ID NO:5 (FIG. 2) and its deoxyuridine derivatives SEQ ID NOS:6-12 (FIG. 3A). Circularization of the aptamers leads to formation of second loop sequence in addition to the conserved loop sequence 5'-TTCTTAGCGTTT-3' (SEQ ID NO:23) used in the examples provided herein. This second loop sequence can be of any length, sequence and sequence composition including the same conserved sequence 5'-TTCTTAGCGTTT-3' (SEQ ID NO:23), and including wherein the second loop sequence portion comprises a nucleotide sequence 5'-TTCT-TAGCGTTT-3' (SEQ ID NO:23) wherein one or more thymidine nucleotides at positions 1, 2, 10, 11, and 12 of the SEQ ID NO:23 sequence are substituted by one or more deoxyuridine nucleotides.

Comparison of the results shown in FIGS. 7B and 7D points to yet another surprising result. First, regardless of the difference in reaction temperature, the same aptamer (SEQ ID NO:12) more efficiently blocked Phusion polymerase at 65° C. than Taq polymerase at 60° C. According to additional surprising aspects of the invention, therefore, the optimal blocking sequence of an aptamer hairpin duplex may be polymerase-specific. Second, the randomly-chosen duplex sequence used in aptamers SEQ ID NOS:5-12 may not be the most optimal one, and it may be further optimized by base pair changes for even better polymerase blockage. Third, using the sequence of aptamer SEQ ID NO:5 as an origin, sequence optimization for strongest DNA polymerase binding can be performed for every DNA polymerase known in the art. In this sense, the present disclosure also provides methods of screening for improved aptamers for use in the disclosed methods.

Aptamers of the invention can contain any number of modified nucleotides, internal and external linker and moieties and other structural modifications as long as these modifications do not interfere with the DNA polymerase deactivation and then activation processes during DNA synthesis. For example, if desirable in a specific assay, they can incorporate phosphorothioate bonds at their termini to protect the aptamers from the exonuclease hydrolysis (Skerra, A., 1992). The hairpin-type noncircular aptamers can contain non-complementary 5' or 3' nucleotide sequences.

Figures 5A, 5B:
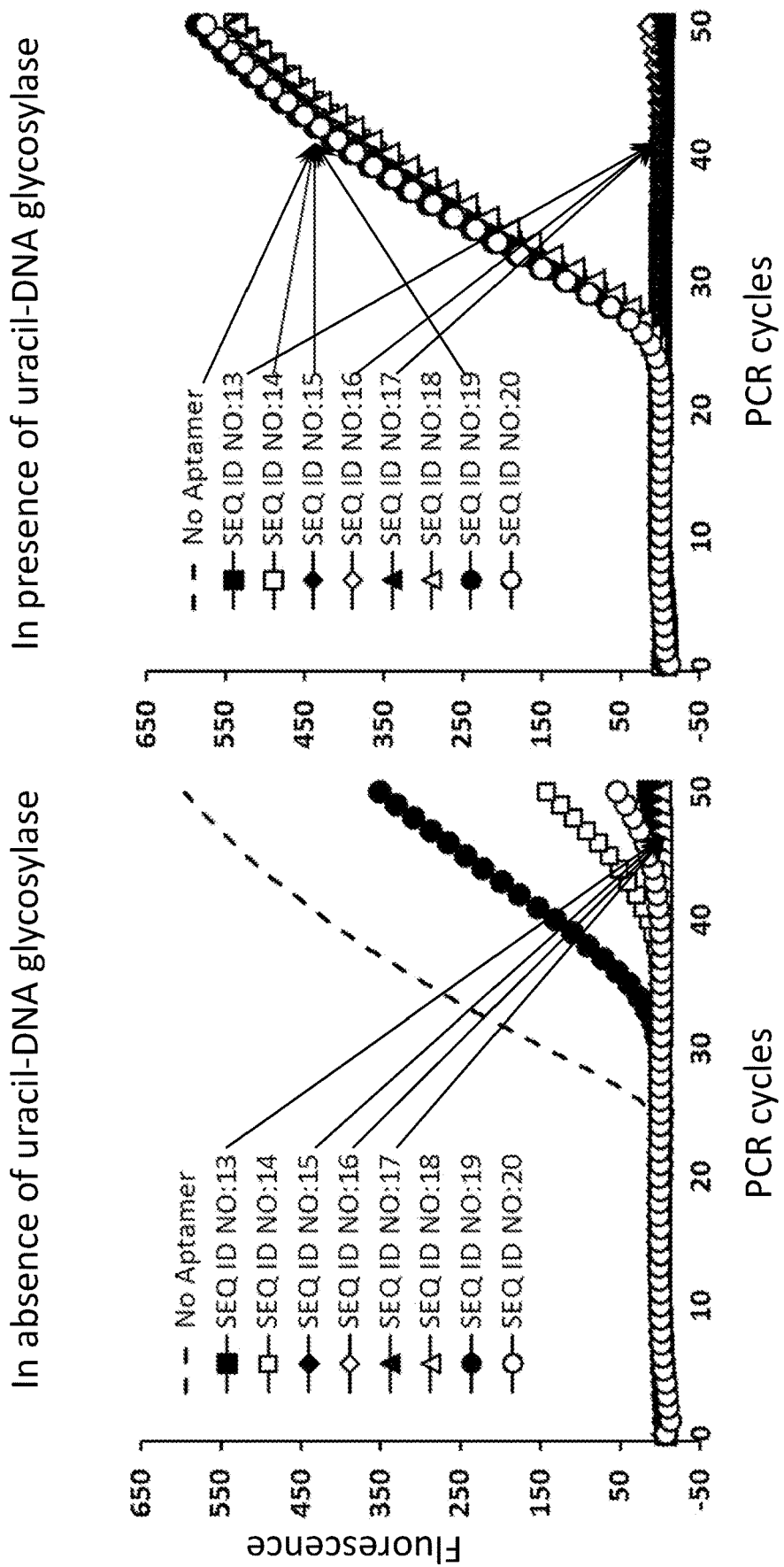
FIGS. 5A and 5B show, according to particular exemplary aspects, the results of fluorescence monitoring of reaction mixtures during PCR (real-time curves) in the presence of the individual aptamers listed in FIG. 4. Sequences of the amplified human β2-microglobulin template, primers and 22-mer FRET probe used in these PCR assays are as shown in FIG. 1. Dashed lines are real-time curves obtained in the absence of any aptamer. Experiments were conducted in the absence (FIG. 5A) or presence (FIG. 5B) of Afu Uracil-DNA Glycosylase. Experimental details are provided below in "Example 3."

Preference should be given to those structural modifications that help to deactivate the DNA polymerase and do not affect the uracil-DNA glycosylase activation reaction. Both loop and stem fragments can be modified in the hairpin-type aptamers. Although the loop segments described in Yakimovich. O. Yu., et al. (2003), Jayasena, S. D. (1999), and U.S. Pat. No. 5,693,502 to Gold, L. and Jayasena, S. D., contain art-recognized conserved sequence motifs, FIGS. 3, 5, and Example 3 herein surprisingly show that removal of the 5-methyl group from deoxythymidine (corresponding modification is deoxyuridine) at certain exemplary positions (SEQ ID NOS:6-12 in FIG. 2 and SEQ ID NOS: 14-20 in FIG. 4) has little or no effect on the aptamer polymerase-inactivation performance (FIGS. 3A and 5A, respectively). Perhaps the most surprising results were obtained in the DNA polymerase-activation assays for noncircular (FIG. 3B) and circular aptamers (FIG. 5B) wherein two pairs of circular (SEQ ID NOS: 16 and 17) and noncircular aptamers (SEQ ID NOS:8 and 9) having deoxyuridines at the same location within the loop sequence did not facilitate reactivation of Taq DNA polymerase in the presence of the uracil-DNA glycosylase. This unexpected phenomenon is discussed herein in Example 3. According to additional aspects of the invention, identification of these two 'glycosylase-insensitive' deoxyuridine positions within the art-recognized highly conserved loop sequence 5'-TTCT-TAGCGTTT-3' (SEQ ID NO:23) has utility for design and functional optimization of both circular and noncircular hairpin-shaped aptamers. Although a single deoxyuridine modification was used in the examples provided herein, more than one nucleotide modification can be successfully applied within the loop sequence, including within the loop sequence 5'-TTCTTAGCGTTT-3' (SEQ ID NO:23), to optimize aptamer properties for DNA polymerase inactivation and activation processes.

Methods of the invention can be performed at any reaction temperatures wherein a DNA polymerase and uracil-DNA glycosylase express suitable activity. Specificity of DNA synthesis is usually increased at higher temperatures, and therefore preference should be given to thermostable enzymes. The upper possible level of the reaction temperature can be selected based on the DNA polymerase stability. In the cases when a uracil-DNA glycosylase is not stable at the desired reaction temperature, the DNA polymerase activation can be initiated at lower intermediate temperature wherein the aptamer-modifying enzyme is stable and active and then raised to the desired reaction temperature. In some embodiments, a DNA polymerase is preferably first deactivated by contacting (e.g., by combining or mixing) with an aptamer before other reaction components of the DNA synthesis are added. Amount of an aptamer used in the reactions is an important factor. Molar reaction concentration of an aptamer applied should be at least equal to the concentration of a DNA polymerase or preferably greater. Market providers commonly do not disclose the molar amount of the enzymes, therefore the precise excess of the aptamers over the DNA polymerases used in Examples provided herein was not known. However, it was anticipated to be in a range of ~40-80 fold, or even greater. In some embodiments, the aptamer is present in a molar excess (ratio) over the DNA polymerases of at least ~10-50 fold, although the ratio can be higher or lower than 10-50 fold. In any case, as will be immediately understood by one of ordinary skill in the art, the amounts of the enzymes, aptamers and other reaction components used in the reaction may be optimized and depend on many factors including, but not limited to selection of the particular enzymes, enzymatic activities at the reaction temperature, reaction temperature itself, nature of the aptamers, etc. Methods of the present invention can be particularly useful for so-called 'fast' PCR with a cycle time shorter than 20 seconds. Rapid cycling requires use of elevated amounts of DNA polymerase and oligonucleotide primers increasing possibility of non-specific reactions.

In certain embodiments, methods of the invention can be practiced using a kit comprising a DNA polymerase-binding oligonucleotide aptamer that is capable of forming a hairpin structure wherein the loop sequence comprises one or more deoxyuridine nucleotides recognizable and modifiable by a uracil-DNA glycosylase enzymatic activity and an uracil-DNA glycosylase to provide for specific modification of the aptamer. The kit can also include a corresponding DNA polymerase which needs to be deactivated by the provided oligonucleotide aptamer. Alternatively, the kit can include, in addition to the aptamer-modifying enzyme, a complex of the DNA polymerase with oligonucleotide aptamer wherein the components of this complex are present at a specific and optimal molar ratio. As a matter of convenience, such kit can include elements allowing the storage, transport and other reaction components such as oligonucleotides, buffering components, additives, reaction enhancers, etc. The aptamers of the kits can be circular or noncircular, and they can incorporate more than one deoxyuridine within their respective loop segments. The kits can be used for DNA synthesis, DNA amplification as well as for detection and/or measurement/quantification of amplified DNA fragments.

In some embodiments, the invention includes a reaction mixture for use in a method of DNA synthesis, which reaction mixture comprises: (i) a DNA polymerase, and (ii) a DNA polymerase-binding hairpin-like oligonucleotide aptamer that incorporates one or more deoxyuridine nucleotide(s) within the loop sequence portion that are modifiable by a uracil-DNA glycosylase enzymatic activity, and wherein the aptamer is present in an amount sufficient to inhibit DNA synthesis activity of the DNA polymerase in the reaction mixture, and other reaction components necessary for DNA synthesis is also a subject of the present invention. The reaction mixtures may also include (iii) a uracil-DNA glycosylase. In some embodiments, the reaction mixture can be assembled using concentrated stock solutions of one or more components, usually in water to provide the desired component concentration in the final mixture. Mixing is recommended to be performed at a low temperature (e.g., close to 0° C.) at which the enzymes, particularly uracil-DNA glycosylases, are inactive. Preferably, the reaction mixture should be used for DNA synthesis soon after preparation. Storage of a fully assembled reaction mixture is not recommended. However, reaction components including enzymes can retain activity for long time (days, months, or even years) in a dried state. For example, in some embodiments of the invention, one or more of the components for forming a mixture of the invention can be provided in a dried form, such as dried beads as described, for example, in U.S. Pat. No. 3,721,725 to Briggs, A. R. and Maxwell, T. J. (1973), including (but are not limited to) DNA polymerase, oligonucleotide aptamer, and uracil-DNA glycosylase(s) such that one or more of the components is prepared in a form of dried beads as described, for example, in U.S. Pat. No. 3,721,725 to Briggs, A. R. and Maxwell, T. J. (1973). In some embodiments, the mixture comprises DNA polymerase, an oligonucleotide aptamer that binds to the DNA polymerase and present in an amount effective to inhibit DNA synthesis activity of the DNA polymerase, and a uracil-DNA glycosylase(s) that is capable of modifying the oligonucleotide aptamer to reduce or eliminate binding of the oligonucleotide aptamer to the DNA polymerase, which are mixed together in a dried form.

Example 1

Synthesis of Aptamers, Primers and Fluorescent Probes

Figure 6:
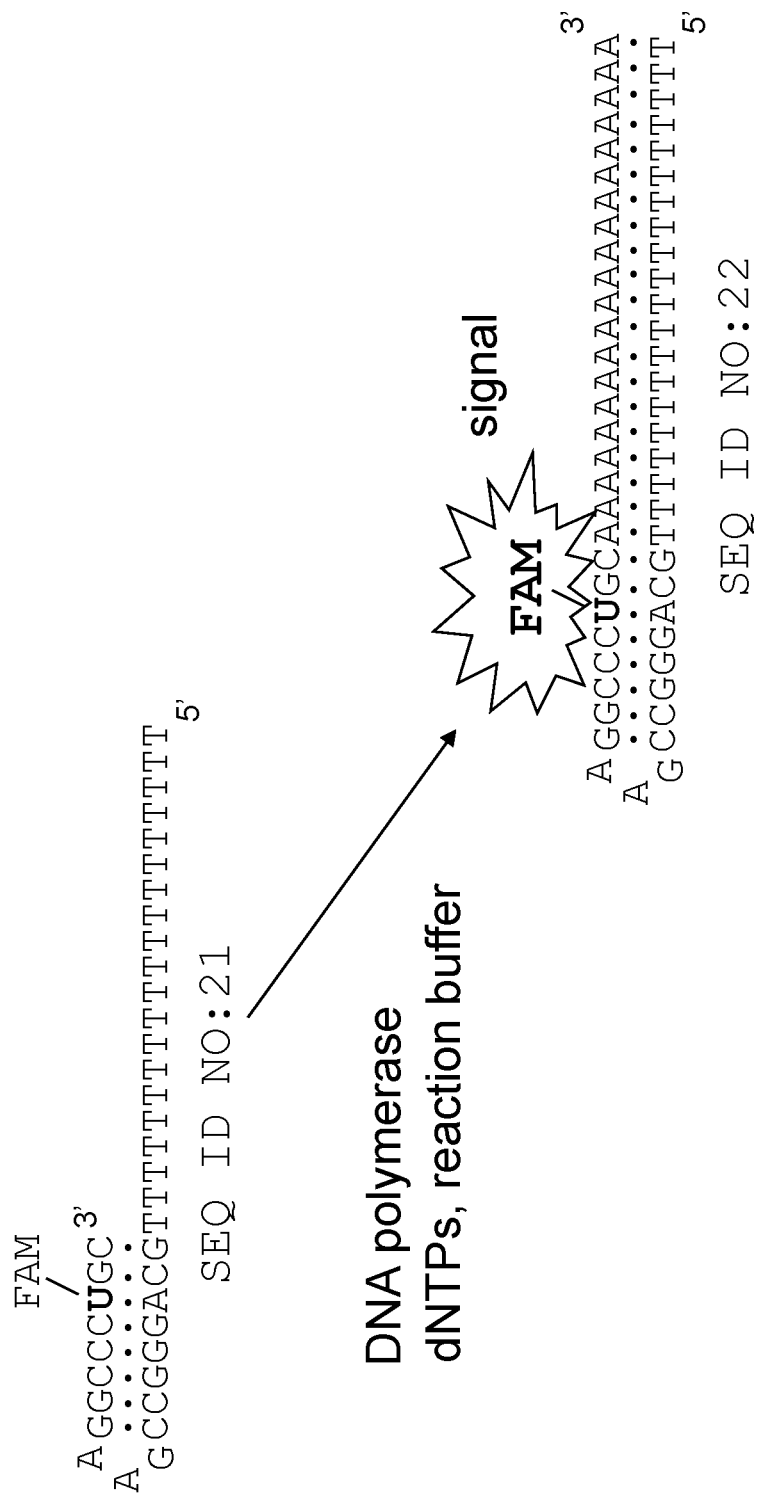
FIG. 6 shows, according to particular exemplary aspects, a scheme of a reaction used in the working Examples to detect and measure DNA polymerase activity. To enable use over a wide range of temperatures (e.g., up to 70° C.), the depicted hairpin-like fluorescent probe was designed to have a G/C-rich stem in the duplex segment and a 5'- . . . GAA . . . hairpin-stabilizing loop (e.g., see Yoshizawa S., et al., 1994). Extension of this hairpin in a reaction buffer in the presence of deoxyribonucleoside 5'-triphosphates (dNTPs) and a DNA polymerase results in a fluorescent signal that directly correlates with the DNA polymerase activity in the reaction.

Standard phosphoramidites, including modified nucleotide analogs such as deoxyuridine (Catalog Number: 10-1050-xx), a phosphoramidite for incorporation of 5'-phosphate moiety, solid supports and reagents to perform the solid support oligonucleotide synthesis were purchased from Glen Research. A 0.25 M 5-ethylthio-1H-tetrazole solution was used as a coupling agent. Oligonucleotides were synthesized either on AB1394 DNA synthesizer (Applied Biosystems) or MerMaid 6 DNA synthesizer (BioAutomation Corporation) using protocols recommended by the manufacturers for 0.2 μmole synthesis scales. Fluorescein (FAM) conjugated to 5-position of deoxyribouridine (U) of probe SEQ ID NO:21 (FIG. 6) was introduced to the hairpin during oligonucleotide synthesis using 5'-dimethoxytrityloxy-5-[N-((3',6'-dipivaloyl fluoresceinyl)-aminohexyl)-3-acrylimido]-2'-deoxyribouridine-3'-[(2-cyanoethyl)-(N,N-diisopropyl)]-phosphoramidite (Glen Research, Catalog Number: 10-1056-xx). A 6-fluorescein reporting dye was incorporated onto the 5'-end, and a BHQI quencher was introduced to the 3'-end of probe SEQ ID NO:3 (FIG. 1) using respective phosphoramidite and CPG from Biosearch Technologies (Catalog numbers: BNS-5025 and BG1-5041G). After the automated synthesis, oligonucleotides were deprotected in aqueous 30% ammonia solution by incubation for 12 hours at 55° C. or 2 hours at 70° C.

Tri-ON oligonucleotides were purified by HPLC on a reverse phase C18 column (LUNA 5 μm, 100 A, 250×4.6 mm, Phenomenex Inc.) using gradient of acetonitrile in 0.1 M triethyl ammonium acetate (pH 8.0) or carbonate (pH 8.5) buffer with flow rate of 1 ml/min. A gradient profile including washing stage 0→14% (10 sec), 14→45% (23 min), 45→90% (10 min), 90→90% (5 min), 90→0% (30 sec), 0→0% (7 min) was applied for purification of all Tri-ON oligonucleotides. The product containing fractions were dried down in vacuum (SPD 1010 SpeedVac, TermoSavant) and trityl groups were removed by treatment in 80% aqueous acetic acid at room temperature for 40-60 min. After addition to the detritylation reaction (100 μl) of 20 μl sodium acetate (3 M), the oligonucleotide components were precipitated in alcohol (1.5 ml), centrifuged, washed with alcohol and dried down. Concentration of the oligonucleotide components was determined based on the optical density at 260 nm and the extinction coefficients calculated for individual oligonucleotides using on-line OligoAnalyzer 3.0 software provided by Integrated DNA Technologies. Based on the measurements, convenient stock solutions in water were prepared and stored at −20° C. for further use. The purity of all prepared oligonucleotide components was confirmed by analytical 8-20% PAAG electrophoresis, reverse phase HPLC and by spectroscopy on Cary 4000 UV-VIS spectrophotometer equipped with Cary WinUV software, Bio Package 3.0 (Varian, Inc.).

Example 2

Synthesis of Circular Oligonucleotide Aptamers

Exemplary circular stem-loop aptamers SEQ ID NOS: 13-20 were prepared by ligation of the corresponding 5'-phosphate incorporating oligonucleotides shown in FIG. 4 using a T4 DNA Ligase kit from New England Biolabs (Catalog number: M0202M). The reaction mixtures were prepared by mixing 67 μl of 10× ligation buffer and 2.5 μl of T4 DNA ligase (2,000 U/μl) from the kit with 10 optical units (at 260 nm) of a 5'-phosphate-labelled oligonucleotide (FIG. 4) and deionized water to provide 670 μl of the final reaction volume. The reaction mixtures were left at room temperature for 1 hour and then heated to 65° C. for 15 min. According to HPLC analysis, the ligation reactions were nearly quantitative (~95%), and the circular aptamers were isolated by HPLC chromatography as described in Example 1. The collected fractions were dried down, and the circular aptamers were dissolved in water. Concentration of the circular aptamers was determined based on the optical density at 260 nm as also described in Example 1. Based on the measurements, convenient stock solutions in water were prepared and stored at −20° C. for further use.

Example 3

Application of Hairpin-Like Aptamers Containing Deoxyuridine Nucleotide within the Loop Sequence to Control Polymerase Activity of Taq Polymerase This working example shows application of hairpin-like aptamers containing deoxyuridine nucleotide within the loop sequence to control activity of Taq polymerase during PCR.

For the results shown in FIGS. 3 and 5, reaction mixtures (25 μL) were prepared on ice by mixing corresponding stock solutions to provide 200 nM forward primer (FIG. 1. SEQ ID NO: 1), 300 nM reverse primer (SEQ ID NO:2), 200 nM FRET probe (SEQ ID NO:3), 0.02 U/μL Taq DNA polymerase (GenScript cat no: E00007), dNTPs (200 μM each), bovine serum albumin (0.1 μg/μL), 100 ng of human genomic DNA (GenScript cat no: M00094) and, when present, one of the aptamers SEQ ID NOS:5-20 (80 nM) in 5 mM $MgCl_2$, 50 mM KCl, 20 mM Tris-HCl (pH8.0). The reaction tubes were quickly transferred into SmartCycler instrument (Cepheid Corporation) and temperature cycling initiated. The PCR time/temperature profile comprised initial incubation at 95° C. for 15 seconds followed by 50 cycles of incubation at 95° C. for 1 second and then at 60° C. for 20 seconds. The reaction fluorescence was measured in every PCR cycle during the annealing/extension stage (60° C.) and the results are shown in FIGS. 3 and 5. Each fluorescence curve is an average of four identical reactions. Initial background fluorescence was subtracted by the instrument software.

The reaction conditions used to generate the fluorescence profiles shown in FIGS. 3 and 5 were identical except for the presence or absence of uracil-DNA glycosylase enzymatic activity and the presence or absence of different oligonucleotides as potential inhibitors of polymerase activity. PCR reactions were performed either in the absence (left panel of each figure) or in the presence (right panel of each figure) of Afu Uracil-DNA Glycosylase (0.016 U/μL, New England Biolabs cat no: M0279S) in the reaction mixtures. Structures of the oligonucleotide aptamers used in the experiments of FIGS. 3 and 5 are shown in FIGS. 2 and 4, respectively.

In summary of this working Example, FIG. 3A shows that the deoxyribouridine nucleotide modification within the hairpin loop (SEQ ID NOS:6-12) does not affect the ability of a noncircular aptamer to deactivate Taq DNA polymerase. All eight aptamers investigated (unmodified SEQ ID NO:5 and modified aptamers SEQ ID NOS:6-12) are very effective in blocking the DNA polymerase during PCR. No fluorescence signal was detected when an aptamer was present in the reaction mixture. Addition of Afu Uracil-DNA Glycosylase effectively removes the DNA polymerase blockage, but not in all cases. As anticipated, unmodified aptamer SEQ ID NO:5 did not respond to the presence of the glycosylase in the reaction mixture. Surprisingly, three out of seven deoxyuridine-modified aptamers, particularly aptamers SEQ ID NOS:8-10 were refractory to DNA polymerase activation by uracil-DNA glycosylase (FIG. 3B), although to different degrees. Aptamers SEQ ID NOS:8 and 9 effectively blocked the DNA polymerase regardless of the presence of glycosylase. In the case of aptamer SEQ ID NO:10, the glycosylase-induced activation of the DNA polymerase was not complete. One possible explanation is that the uracil-DNA glycosylase cannot cleave the uracil base at those specific loop locations of aptamers SEQ ID NOS:8 and 9, and that there is a somewhat reduced rate of the uracil cleavage for aptamer SEQ ID NO: 10. This hypothesis is supported by the art-recognized fact that loop sequences in hairpin-shaped oligonucleotides, especially short ones as in the aptamers exemplified herein, are structurally constrained, and this might explain by some of the nucleotides are inaccessible or partially accessible for recognition by nucleases, glycosylases and other DNA-modifying enzymes. The particular loop sequence 5'TTCT-TAGCGTTT3' (SEQ ID NO:23) used in design of the hairpin aptamers herein is known in the art to be highly conserved (e.g., Yakimovich, O. Yu., et al. (2003), Jayasena S. D. (1999), and U.S. Pat. No. 5,693,502 to Gold, L. and Jayasena, S. D.). However, according to surprising aspects of the present invention, this sequence conservation does not exclude a possibility that loss of the substituted bases at the aptamer loop locations discussed herein provides for retention of the DNA polymerase-inactivating capabilities in the case of aptamers SEQ ID NOS:8 and 9 and partially in the case of SEQ ID NOS: 10.

The circular hairpin-shaped aptamers SEQ ID NOS: 13-20 shown in FIG. 4 were also investigated in PCR assays (FIGS. 5A and 5B) as ligands for reversible inactivation of Taq DNA polymerase. Regardless of shorter stem lengths (14 base pairs for SEQ ID NOS: 13-20 vs. 17 base pairs for SEQ ID NOS:5-12) and highly elevated A-T base pair content, many of these circular aptamers effectively blocked Taq DNA polymerase during PCR (FIG. 5A). Only three aptamers, in particular SEQ ID NOS: 14, 19, and 20 provided incomplete inactivation of the polymerase, where aptamer SEQ ID NO:19 provided the least inhibitory effect. Since unmodified circular aptamer SEQ ID NO: 13 was very effective in polymerase blockage, the PCR results obtained for aptamers SEQ ID NOS:14, 19, and 20 (FIG. 5A) indicate a likely positive hydrophobic contribution to aptamer-DNA polymerase complex formation, that is mediated by the 5-methyl group of thymine, which is absent at the corresponding deoxyuridine-modified locations within the loop sequence. The set of circular aptamers SEQ ID NOS: 13-20 revealed glycosylase-induced polymerase reactivation patterns (FIG. 5B) similar to that observed for noncircular aptamers SEQ ID NOS:5-12 (FIG. 3B), with one exception. Unlike its counterpart noncircular aptamer SEQ ID NO: 10 (FIG. 3B), circular aptamer SEQ ID NO: 18 effectively provided for reactivation of the inactivated DNA polymerase in the presence of uracil-DNA glycosylase.

Example 4

Kinetics of Activation by Uracil-DNA Glycosylase of Various DNA Polymerases Initially Blocked by Deoxyuridine-Containing Aptamer This working example shows the kinetics of activation by uracil-DNA glycosylase of Taq (GenScript cat no: E00007), Q5® (New England Biolabs cat no: M0491S), Vent® (New England Biolabs cat no: M0254S), Deep Vent® (New England Biolabs cat no: M0258S), Bst large fragment (New England Biolabs cat no: M0275S), and Phusion® (New England Biolabs cat no: M0530S) DNA polymerases initially blocked by a deoxyuridine-containing aptamers.

For FIG. 7, reaction mixtures (25 μL) were prepared on ice by mixing corresponding stock solutions to provide self-priming hairpin SEQ ID NO:21 (200 nM, FIG. 6), a DNA polymerase (0.008 U/μL), dNTPs (200 μM each), bovine serum albumin (0.1 μg/μL) and, when present, the noncircular aptamer SEQ ID NO:12 (80 nM, FIG. 2) and Afu Uracil-DNA Glycosylase (0.016 U/μL, New England Biolabs cat no: M0279S) in 5 mM $MgCl_2$, 50 mM KCl, 20 mM Tris-HCl (pH8.0). During preparation of the reaction mixture, the self-priming hairpin (SEQ ID NO:21) and uracil-DNA glycosylase were always added last to a premixed solution. Then the reaction tubes were transferred into a SmartCycler instrument (Cepheid Corporation) and heated to 60 or 65° C. as indicated for each fluorescence profile in FIG. 7. The reaction fluorescence was monitored every 7 seconds. The plotted curves are the averages of four paralleled identical reactions. Initial background fluorescence was subtracted.

The results of FIG. 7 show that not only Taq polymerase, but also many other DNA polymerases can be inactivated and then activated using aptamers of the present invention in the presence of uracil-DNA glycosylase. Only one of six investigated exemplary DNA polymerases, particularly Bst DNA polymerase, was not inactivated by noncircular aptamer SEQ ID NO: 12.

Other DNA polymerases showed an inactivation in the presence of this aptamer as well as gradual uracil-DNA glycosylase-induced activation, although the efficiency of both processes was variable among the individual DNA polymerases.

References cited, and incorporated herein for their respective teachings:

Cleuziat, P., and Mandrand, B., "Method for amplifying nucleic acid sequences by strand displacement using DNA/RNA chimeric primers," 1998, U.S. Pat. No. 5,824,517.

Dattagupta, N., Stull, P. D., Spingola, M., and Kacian, D. L., "Isothermal strand displacement nucleic acid amplification," 2001, U.S. Pat. No. 6,214,587.

Davey, C., and Malek, L. T., "Nucleic acid amplification process," 2000, U.S. Pat. No. 6,063,603.

Eckstein, F., ed., (1991) Oligonucleotides and Analogs: A Practical Approach. Oxford University Press, New York.

Hedgpeth, J., Afonina, I. A., Kutyavin, I. V., Lukhtanov, E. A., Belousov, E. S., and Meyer, Jr., R. B., "Hybridization and mismatch discrimination using oligonucleotides conjugated to minor groove binders," 2010, U.S. Pat. No. 7,794,945.

Gait, M. J., ed., (1984) *Oligonucleotide Synthesis: A Practical Approach*, IRL Practical Approach Series, IRL Press, Oxford.

Gold, L. and Jayasena, S. D., "Nucleic acid ligand inhibitors to DNA polymerase," 1997, U.S. Pat. No. 5,693,502.

Jayasena, S. D., "Aptamers: An emerging class of molecules that rival antibodies in diagnostics," *Clinical Chemistry* 45:1628-1650, 1999.

Kornberg, A., and Baker, T. (1992) DNA Replication, Second Edition, W. H. Freeman and Company, New York.

Kurn, N., "Methods and compositions for linear isothermal amplification of polynucleotide sequences, using a RNA-DNA composite primer," 2001, U.S. Pat. No. 6,251,639.

Kutyavin, I. V., and Lukhtanov, E. A., Gamper. H. B., Meyer, Jr., R. B., "Covalently linked oligonucleotide minor grove binder conjugates," 1998, U.S. Pat. No. 5,801,155.

Kutyavin, I. V., "Use of base-modified deoxynucleoside triphosphates to improve nucleic acid detection," 2013, U.S. Pat. No. 8,349,556.

Lehninger, A. L. (1975) *Biochemistry,* 2nd edition. New York, Worth Publishers, Inc.

Lizardi, P., "Rolling circle replication reporter systems," 1998, U.S. Pat. No. 5,854,033.

Meyer, Jr., R. B., Afonina, I. A., and Kutyavin, I. V., "Oligonucleotides containing pyrazolo[3,4-D]pyrimidines for hybridization and mismatch discrimination," 2000, U.S. Pat. No. 6,127,121.

Mullis. K. B., "Process for amplifying nucleic acid sequences," 1987. U.S. Pat. No. 4,683,202.

Mullis, K. B., Erlich, H. A., Arnheim, N., Horn, G. T., Saiki, R. K., and Scharf, S. J., "Process for amplifying, detecting, and/or-cloning nucleic acid sequences," 1987, U.S. Pat. No. 4,683,195.

Notomi, T., and Hase, T., "Process for synthesizing nucleic acid," 2002, U.S. Pat. No. 6,410,278.

Paul, N., Shum, J., and Le. T. (2010), Hot start PCR. In King N. (ed.), *RT-PCR Protocols: Second Edition*. Methods in Molecular Biology, Springer Science+Business Media. LLC, V. 630:301-318.

Sambrook, J., et al. (1989), *Molecular Cloning: A Laboratory Manual,* 2nd Edition. Cold Spring Harbor Lab. Cold Spring Harbor, N.Y.

Skerra, A., "Phosphorothioate primers improve the amplification of DNA sequences by DNA polymerases with proofreading activity," *Nucleic Acids Res.* 20:3551-3554, 1992.

Walker, G. T., Little, M. C., and Nadeau, J. G., "Nucleic acid target generation," 1993, U.S. Pat. No. 5,270,184.

Yakimovich, O. Yu., Alekseev, Ya. I., Maksimenko, A. V., Voronina, O. L., and Lunin, V. G., "Influence of DNA aptamer structure on the specificity of Binding to Taq DNA polymerase," *Biochemistry (Moscow)* 68:228-235, 2003.

Yoshizawa. S., Ueda, T., Ishido, Y., Miura, K., Watanabe, K., and Hirao, I., "Nuclease resistance of an extraordinarily thermostable mini-hairpin DNA fragment, d(GC-GAAGC) and its application to in vitro protein synthesis," *Nucleic Acids Res.* 22:2217-2221, 1994.

The invention claimed is:

1. A method for activating an aptamer-inactivated DNA polymerase, comprising:
   providing a reaction mixture suitable for DNA synthesis, the reaction mixture comprising (i) a DNA polymerase, (ii) a uracil-DNA glycosylase enzymatic activity, and (iii) a DNA polymerase-binding oligonucleotide aptamer that comprises a hairpin structure having a stem sequence portion and a loop sequence portion, wherein the loop sequence portion comprises one or more deoxyuridine nucleotide(s) modifiable by the uracil-DNA glycosylase enzymatic activity, and the aptamer is present in an amount sufficient to inhibit DNA synthesis activity of the DNA polymerase in the reaction mixture; and
   modifying the aptamer by the uracil-DNA glycosylase enzymatic activity to form a modified aptamer having less or no inhibitory effect on the DNA polymerase, thereby activating or enhancing the DNA synthesis activity of the DNA polymerase, to start and/or increase DNA synthesis in the reaction mixture.

2. The method of claim 1, wherein modifying the aptamer is facilitated by use of a reaction temperature that facilitates both the DNA polymerase activity and the uracil-DNA glycosylase enzymatic activity.

3. The method of claim 1, wherein modifying the aptamer is facilitated by increasing the temperature of the reaction mixture from a first temperature to a second temperature that activates or more strongly facilitates the uracil-DNA glycosylase enzymatic activity.

4. The method of claim 1, wherein providing the reaction mixture comprises dissolving a dried form of at least one of the (i) DNA polymerase, (ii) oligonucleotide aptamer, and (iii) uracil-DNA glycosylase enzymatic activity, into an aqueous solution.

5. The method of claim 1, wherein the DNA synthesis results in DNA amplification in the reaction mixture.

6. The method of claim 5, wherein the DNA amplification is an isothermal amplification reaction.

7. The method of claim 5, wherein the DNA amplification is PCR.

8. The method of claim 5, comprising detecting the presence of a target DNA in the reaction mixture.

9. The method of claim 5, comprising measuring an amount of a target DNA in the reaction mixture.

10. The method of claim 1, wherein the oligonucleotide aptamer is circular.

11. The method of claim 1, wherein the uracil-DNA glycosylase enzymatic activity is effective to modify the oligonucleotide aptamer by generating at least one abasic site within the loop sequence portion.

12. The method of claim 1, wherein the uracil-DNA glycosylase comprises Afu Uracil-DNA Glycosylase.

13. The method of claim 1, wherein the loop sequence portion comprises a nucleotide sequence 5'-TTCTTAGCGTTT-3' (SEQ ID NO:23) wherein one or more thymidine nucleotides at positions 1, 2, 10, 11, and 12 of the SEQ ID NO:23 sequence are substituted by one or more deoxyuridine nucleotides.

* * * * *